United States Patent
Tafti

(10) Patent No.: US 11,712,487 B2
(45) Date of Patent: Aug. 1, 2023

(54) COMPOSITE EMBOLIZATION BEADS

(71) Applicant: RAIKA MEDICAL IMAGING INC., Encino, CA (US)

(72) Inventor: Bashir Akhavan Tafti, Los Angeles, CA (US)

(73) Assignee: RAIKA MEDICAL IMAGING INC., Encino, CA (US)

( * ) Notice: Subject to any disclaimer, the term of this patent is extended or adjusted under 35 U.S.C. 154(b) by 554 days.

(21) Appl. No.: 16/728,230

(22) Filed: Dec. 27, 2019

(65) Prior Publication Data
US 2020/0138988 A1 May 7, 2020

Related U.S. Application Data

(63) Continuation-in-part of application No. PCT/US2018/039965, filed on Jun. 28, 2018.

(60) Provisional application No. 62/525,796, filed on Jun. 28, 2017.

(51) Int. Cl.
| A61K 51/12 | (2006.01) |
| A61K 49/18 | (2006.01) |
| A61K 9/51 | (2006.01) |
| A61N 5/10 | (2006.01) |

(52) U.S. Cl.
CPC .......... *A61K 51/1251* (2013.01); *A61K 9/51* (2013.01); *A61K 49/1887* (2013.01); *A61N 5/10* (2013.01); *A61N 2005/109* (2013.01)

(58) Field of Classification Search
None
See application file for complete search history.

(56) References Cited

U.S. PATENT DOCUMENTS

| 2003/0120355 A1 | 6/2003 | Hafeli | |
| 2011/0301452 A1* | 12/2011 | Maschke | A61B 34/73 424/452 |
| 2012/0123189 A1 | 5/2012 | Ribbing | |
| 2014/0193331 A1* | 7/2014 | Naczynski | A61K 49/0019 424/9.1 |
| 2015/0147276 A1 | 5/2015 | Ingber | |
| 2016/0213793 A1 | 7/2016 | Goodman | |

OTHER PUBLICATIONS

Barth, et al. "Current status of boron neutron capture therapy of high grade gliomas and recurrent head and neck cancer," Radiation Oncology, 2012, 7:146.
Brechbiel, M. W., "Bifunctional chelates for metal nucleides," QJ Nucl. Med. Mol. Imaging, 2008, 52:166-173.
M.F. Maitz, "Applications of synthetic polymers in clinical medicine", Biosurface and Biotribology, 2015, 1, 161-176.
Vroman, I. and Tighzert, L., "Biodegradable Polymers," Materials, 2009, 2, 307-344.
Vaidya S, Tozer KR, Chen J., "An overview of embolic agents," Semin Intervent Radiol. Sep. 2008;25(3):204-15.

* cited by examiner

*Primary Examiner* — Jennifer L Chin
(74) *Attorney, Agent, or Firm* — Clark & Elbing LLP

(57) ABSTRACT

The present invention relates to compositions and methods for imaging and treating various diseases and disorders, including cancers. The composition of the invention can include a plurality of biodegradable micro-beads, each embedding a plurality of nano-beads, further including a polymer, a radionuclide, a radionuclide chelator, a radioligand, a chemotherapeutic agent, and a cell-penetrating peptide. Upon injection into a blood vessel supplying a cancer tumor, the micro-beads lodge into the tumor and degrade, releasing the nano-beads with a therapeutic or diagnostic agent. The compositions and methods of the invention provide a more homogeneous and deeper distribution of radiation or chemotherapeutic agents throughout the target tumor. The micro-beads provide a local, sustained, and controlled delivery nano-beads including therapeutic or diagnostic agents.

21 Claims, 6 Drawing Sheets

COMPOSITE EMBOLIZATION BEADS

CROSS-REFERENCE TO RELATED APPLICATIONS

The present application is a continuation-in-part under 35 U.S.C. § 111(a) of International Application No. PCT/US2018/039965, filed Jun. 28, 2018, which claims priority to U.S. Provisional Application No. 62/525,796, filed Jun. 28, 2017, all of which are incorporated by reference herein in their entireties.

BACKGROUND OF THE INVENTION

Embolization therapy is a minimally invasive treatment that involves the use of a catheter to inject embolic agents such as synthetic materials, spherical beads, coils, balloons, detachable plugs, or medications, into a blood vessel to prevent blood flow to an area (Vaidya, et al., 2008, Semin Intervent Radiol, 25(3) 204-215). For example, catheter-directed embolization can be used to block vessels supplying blood to a malignant tumor causing the tumor cells to die. Currently there are a few known methods of treating patients with malignant tumors using transarterial embolization. These methods are bland embolization, chemoembolization and radioembolization. Transarterial bland embolization involves the use of a catheter to inject synthetic materials such as small spherical glass beads into the blood vessels that are supplying malignant tumor cells. The application of these beads diminishes the supply of blood to these tumors and cause the malignant cells to die. Chemoembolization, also known as trans-arterial chemoembolization, is similar to bland embolization, but the surface of the beads is coated with a chemotherapeutical drug such as Doxorubicin. This technique can also be performed by solely administering chemotherapeutic agents directly into the blood vessels, after which the artery is plugged. In radioembolization, sometimes known as trans-arterial radioembolization, unlike chemoembolization, the small beads (a.k.a microspheres) are coated or loaded with a radioactive isotope. Once the beads are injected and lodged within the tumor vasculature, they emit small amounts of radiation and therefore destroy the malignant tumor cells within a given proximity. Although these various types of treatment described above have greatly increase the survival rate in patients that have been diagnosed with early onset of HCC, there are still many drawbacks (Bilbao et al., 2009, Semin Intervent Radiol, 126-142). For example, Polyvinyl alcohol particles, which have been used in embolization procedures can vary in size and are irregular in shape. When administered to patients, these particles have been known to aggregate, which leads to the occlusion of more proximal vessels and therefore, the more distal vessels remain open leading to suboptimal outcomes. The clumping of these particles can also cause altered biodistribution and lead to non-target embolization (Vaidya, et al., Semin Intervent Radiol, 25(3) 204-215).

Liver cancer has one of the highest mortality rates in the world, behind lung cancer (Altekruse et al., 2009, JCO, 27(9): 1485-1491). Among the most common types of liver cancer is Primary Hepatic Carcinoma or Hepatocellular Carcinoma (HCC) (London W T et al., 2006, Oxford University Press, ed(3): 763-786, (Altekruse et al., 2009, JCO, 27(9): 1485-1491). In adults, most HCC is caused by an infection such a hepatitis (B or C), or caused by the onset of cirrhosis. HCC can also develop in patients that have a metabolic syndrome, hemochromatosis or have eaten foods tainted with aflatoxin (F. G. Peers et al., 1973, BJC, 27(6): 473-484). Most often, HCC begins as a single tumor, but if left untreated, can spread to other parts of the liver, and other parts of the body. Although there has been a huge advancement in methods of treating HCC, the survival rate remains relatively low (Ref. American Cancer Society webpage)

Liver cancer can be categorized into several stages, ranging from stage I, which is the least severe, to stage IVB which is the most advanced (American Cancer Society. Cancer Facts & Figures 2016. Atlanta, Ga.: American Cancer Society; 2016). In some cases, if detected early, surgery or liver transplants can be performed with curative intent. However, in some cases liver tumors cannot be removed by surgery or are too lager to be treated by techniques such as ablation. Tumor specific targeting therapy is a very effective means of destroying malignant cells (Dharap et al., 2005, PNAS, 102(36) 12962-12967). One of the main disadvantages of typical cancer chemotherapy is the effect that many anticancer drugs have on normal or healthy tissue. Embolization is an alternative method of treating patients with liver tumors and is particularly effective in combating larger liver tumors, that cannot be removed by surgery (Bilbao et al., 2009, Semin Intervent Radiol, 126-142). Embolization therapy can be used to specifically target these malignant cells, because most normal living liver cells receive blood through the portal vein, whereas malignant liver cells are supplied via the hepatic artery. Thus, administration of therapeutic agents through the hepatic arterial system allows for normal liver cells to be unaffected or harmed by the administered treatment.

The use of glass micro-beads and synthetic particles in embolization procedures has been well established and has been shown to be an effective method in treating HCC. However, the use of these embolic agents do not come without their share of flaws. For example, variations in size of the microspheres can result in occlusion of the more proximal vessels with larger beads and prevent the smaller beads from reaching the deep tumor vasculature. This partial treatment, in turn, will often lead to the recurrence of the cancer tissue. Lack of visualization (i.e. inability to be seen using common imaging modalities such as x-ray fluoroscopy, CT, and MRI) is another limitation of the current microspheres. As a result, the physicians may not be able to accurately track the distribution of microspheres. The latter in turn can cause suboptimal treatment of the tumors or lead to over treatment and non-target embolization (i.e. embolization of normal tissues). Lack of visualization can also reduce accuracy of post-operative imaging for follow up. Additionally, microspheres are often made of non-biodegradable materials such as glass, and can remain in the patients' blood vessels indefinitely (Vaidya, et al., Semin Intervent Radiol, 25(3) 204-215).

There is a need in the art for novel and improved embolization methods and compositions, as well as improved methods of treating cancer, such as HCC and other liver cancers. The present invention meets this need.

SUMMARY OF THE INVENTION

In one aspect, the invention relates to a micro-bead comprising: a matrix; and a plurality of nano-beads; wherein the nano-beads further comprise at least one selected from the group consisting of a polymer, a radionuclide, a radionuclide chelator, a ligand, a chemotherapeutic agent, color pigments, and a cell-penetrating peptide. In one embodiment, the matrix comprises a polymer selected from the group consisting of polyglycolic acid (PGA), polylactic acid (PLA), poly(lactic-co-glycolic acid) (PLGA), polycaprolactone (PCL), collagen, gelatin, glass, polymethylmethacrylate (PMMA), and polystyrene. In one embodiment, the polymer is selected from the group consisting of poly (methyl methacrylate) (PMMA), polystyrene, carboxymethyl chitosan (CCN), PLGA, and carboxymethyl cellulose (CMC).

In one embodiment, the nano-beads comprise a biodegradable polymer. In one embodiment, the nano-beads comprise a non-biodegradable polymer. In one embodiment, the nano-beads comprise a radionuclide that is a radioactive isotope of an element selected from the group consisting of actinium, astatine, bismuth, cesium, chromium, cobalt, dysprosium, erbium, holmium, iodine, iridium, iron, lead, lutetium, lutetium, molybdenum, palladium, phosphorus, potassium, radium, rhenium, samarium, selenium, sodium, strontium, sulfur, technetium, tritium, xenon, ytterbium, yttrium, carbon, nitrogen, oxygen, fluorine, copper, gallium, germanium, indium, krypton, rubidium, strontium, and thallium. In one embodiment, the radionuclide chelator is selected from the group consisting of triethylenetetramine (TETA), 1,4,7-triazacyclononane-1,4,7-trisacetic acid (NOTA), and 1,4,7,10-tetraazacyclododecane-1,4,7,10-tetraacetic acid (DOTA). In one embodiment, the ligand is selected from the group consisting of [$^{18}$F]altanserin, [$^{18}$F]setoperone, [$^{18}$F]ketanserin, [$^{18}$F]flumazenil, [$^{11}$C]3-amino-4-(2-dimethylaminomethylphenylsulfanyl)-benzonitrile ([$^{11}$C]DASB), [$^{11}$C]raclopride, [$^{123}$I]Ioflupane, and [$^{123}$I]Altropane. In one embodiment, the nano-beads comprise an MRI contrast agent, gold nanoparticles, color pigments, a PET contrast agent, or a radiopaque contrast agent.

In one embodiment, the nano-beads further comprise boron-10 or gadolinium-157. In one embodiment, the chemotherapeutic agent is selected from the group consisting of doxorubicin, cisplatin, taxol, vinblastine, vincristine, bleomycin, fluorouracil, methotrexate, bortezomib, and etoposide. In one embodiment, the cell-penetrating peptide is selected from the group consisting of R9, TAT, HSV, gH625, penetratin, VP22, Xentry, and transportan.

In one aspect, the present invention relates to a micro-bead comprising a biodegradable matrix; and a sub-microbead embedded in the biodegradable matrix; wherein the biodegradable matrix comprises at least one of a biodegradable polymer, radionuclide, a radionuclide chelator, a ligand, a chemotherapeutic agent. In one embodiment, the biodegradable matrix further comprises a plurality of nano-beads. In one embodiment, the micro-bead further comprises a separation layer between the sub-microbead and the biodegradable matrix, wherein the separation layer comprises at least one lipid.

In one aspect, the present invention relates to a method of treating a disease or disorder in a subject, comprising the step of administering to the subject a composition comprising a plurality of micro-beads of the present invention. In one embodiment, the micro-beads degrade over a period of time between 1 and 90 days. In one embodiment, the disease or disorder is cancer. In one embodiment, the cancer is selected from the group consisting of primary renal cell carcinoma (RCC), primary hepatocellular carcinoma (HCC), and liver metastatic lesions from other primary cancers. In one embodiment, the primary cancers are selected from the group consisting of gastric cancer, colorectal cancer, breast cancer, pancreatic cancer, lung cancer, and prostate cancer.

In one aspect, the present invention relates to a method of treating cancer in a subject in need thereof, the method comprising the steps of administering to the subject the micro-beads of the present invention; and exposing the subject to a neutron source.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

DETAILED DESCRIPTION

Figure 1:
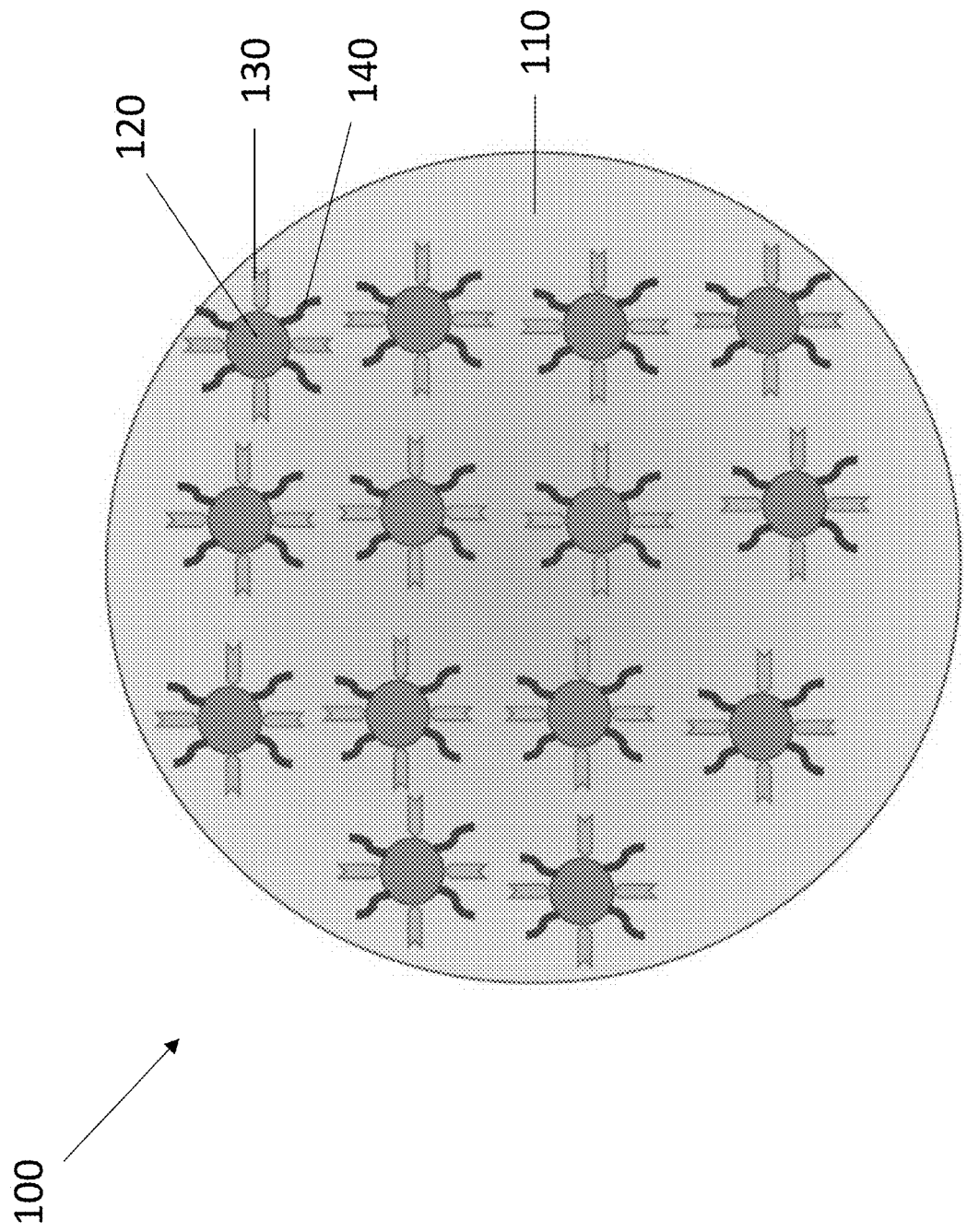
FIG. 1 is a schematic depicting an exemplary composite micro-bead comprising a plurality of nano-beads according to an aspect of the invention. Note that FIG. 1 is not to scale.

The invention provides novel compositions and methods useful in embolization therapy, such as micro-beads including a biodegradable polymer matrix and a plurality of nano-beads embedded in the matrix, or appended on the surface of the micro-bead. The nano-beads are also made from a polymeric material, and further comprise a variety of functional elements such as radionuclides, ligands, chelating moieties, chemotherapeutic agents, cell-penetrating peptides, or neutron capturing atoms such as boron or gadolinium.

Definitions

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The terms "patient," "subject," "individual," and the like, are used interchangeably herein, and refer to any animal, including mammals. In certain non-limiting embodiments, the patient, subject, or individual is a human.

As used herein, the term "composition" or "pharmaceutical composition" refers to a mixture of at least one micro-bead of the invention with other chemical components, such as carriers, stabilizers, diluents, dispersing agents, suspending agents, thickening agents, and/or excipients. The pharmaceutical composition facilitates administration of the micro-beads to an organism.

A "disease" is a state of health of an a subject wherein the subject cannot maintain homeostasis, and wherein if the disease is not ameliorated, the subject's health continues to deteriorate. In contrast, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health. As used herein, "treating a disease or disorder" means reducing the frequency and/or severity with which a symptom of the disease or disorder is experienced by an individual.

The term "treat," as used herein, means reducing the frequency and/or severity of a sign or symptom of a disease or disorder experienced by a subject. Thus, "treat" and "treating" are not limited to the case where the subject (e.g., patient) is cured and the disease or disorder is eradicated. Rather, the present invention also contemplates treatment that merely reduces signs or symptoms, improves (to some degree) and/or delays disease or disorder progression. The term "treatment" also refers to the alleviation, amelioration, and/or stabilization of signs or symptoms, as well as a delay in the progression of signs or symptoms of a disease or disorder. As used herein, to "alleviate" a disease or disorder means to reduce the frequency and/or severity of one or more signs and/or symptoms of the disease or disorder.

The term "effective amount" in a subject, as used herein, refers to an amount that provides a therapeutic or prophylactic benefit in the subject. The term "therapeutically effective amount" refers to the amount of the compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the signs and/or symptoms of the disease or disorder being treated. The therapeutically effective amount will vary depending on the compound, the disease or disorder, the severity of the disease or disorder, and the age, weight, etc., of the subject to be treated.

The term "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound, molecule, micro-bead or nano-bead useful within the invention, within or to the patient such that it may perform its intended function.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Compositions of the Invention

Referring now to FIG. 1, in one aspect, the invention relates to an embolization micro-bead 100 comprising a matrix 110 and a plurality of nano-beads 120.

Figure 2:
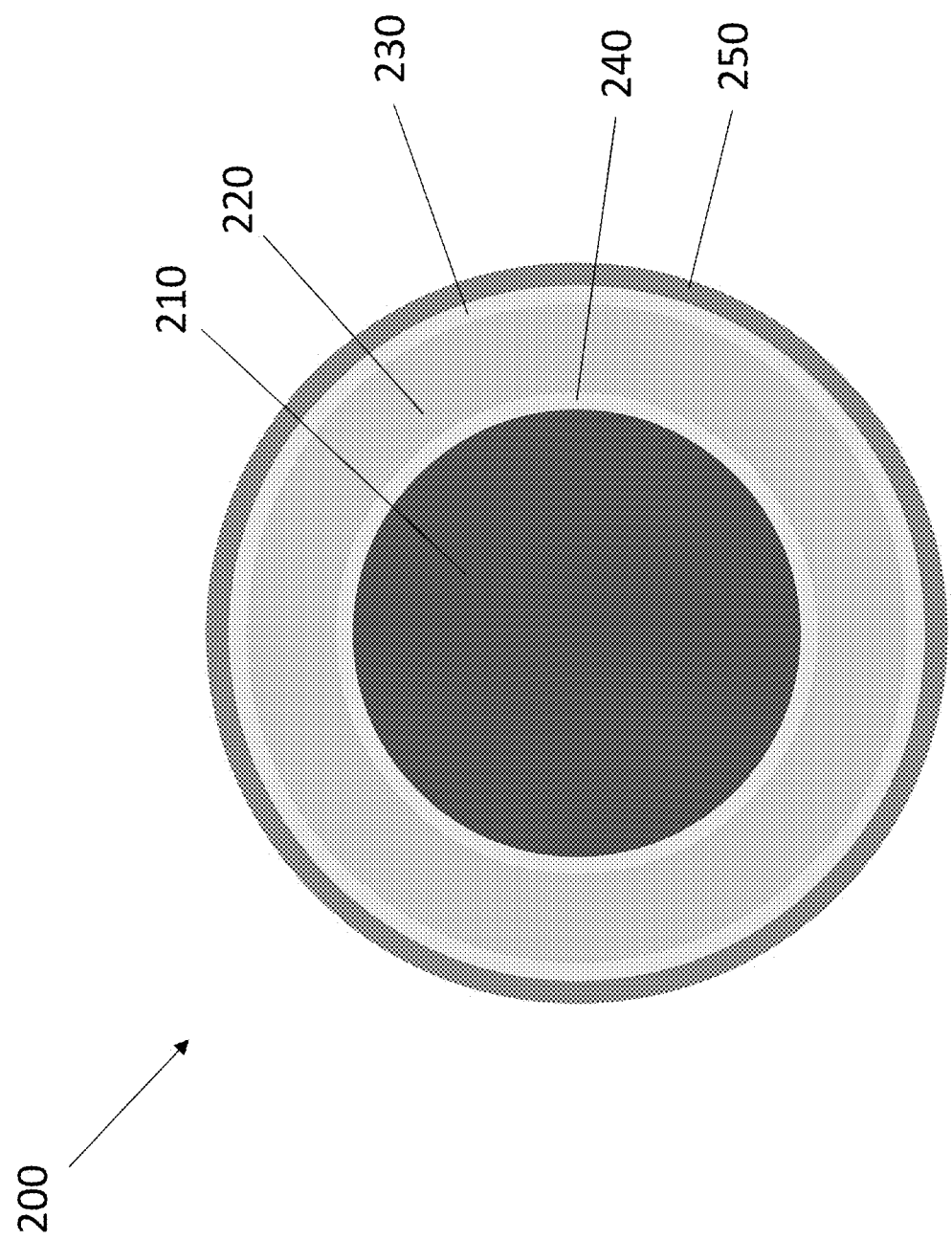
FIG. 2 is a schematic depicting exemplary composite micro-beads comprising a sub-microbead according to an aspect of the invention. Note that FIG. 2 is not to scale.

Referring now to FIG. 2, in one aspect, the invention relates to a micro-bead 200 comprising a sub-micro-bead 210, biodegradable matrix 220, optional separation layers 230 and 240, and optional coating layer 250.

In some embodiments, the matrix binds the nano-beads. In one embodiment, the nano-beads are embedded in a matrix.

In one embodiment, the matrix is a biodegradable matrix. In one embodiment, biodegradation of the biodegradable matrix results in release of the nano-beads. In one embodiment, control of the biodegradable matrix composition may control the rate of release of the nano-beads. In one embodiment, the biodegradable matrix comprises at least one biodegradable polymer. Exemplary biodegradable polymers include, but are not limited to, Polyglycolide (PGA), Polylactide (PLA), Poly(lactide-co-glycolide) (PLGA), Polycaprolactone (PCL), Poly(alkenedicarboxylate) polymers such as Poly(butylene succinate) (PBS), poly(ethylene succinate) (PES), poly(butylene succinate-co-adipate) (PBSA), Poly(p-dioxanone) (PPDO), Polycarbonates such as Poly(trimethylene carbonate) (PTMC), Poly(propylene carbonate), poly[oligo(tetramethylene succinate)-co(tetramethylene carbonate)], aromatic copolyesters such as poly(butylene adipate-co-terephtalate) (PBAT), poly(ethylene terephtalate), Biomax®, Ecoflex®, Origo-Bi®, poly(β-hydroxyalcanoate), xanthan, curdlan, pullulan, Poly(hydroxybutyrate) (PHB), and Poly(hydroxybutyrate-co-hydroxyvalerate) (PHBV), polyamides/polypeptides such as Aliphatic poly(ester-amide)s, copolymers of 1,2-ethanediol, adipic acid and amino acids, including glycine and phenylalanine, Cameo®, and Bak 1095®, polyanhydrides such as poly(sebacic anhydride) and copolymers comprising carboxyphenoxypropane, Polysaccharides such as Chitin, chitosan, Starch, poly-α-1,4-D-glucopyranoside (amylose), poly-α-1,4-Dglucopyranoside-α-1,6-D-glucopyranoside (amylopectine), Cellulose, Cellulose esters, Cellulose acetate, microcrystalline cellulose, carboxymethylcellulose, lignocellulose, Alginic acid, sodium alginate, calcium alginate, hyaluronic acid, chondroitin sulphate, proteins such as gelatin, soy protein, oils, fatty acids, Methyl methacrylate and poly(ethyl acrylate) gelatine grafts, Elastin, albumine, fibrin, wheat gluten, and collagen, polymer blends such as Starch-poly(ethylene-co-vinyl alcohol) (EVOH), Starch-polyvinyl alcohol, Starch-PLA, Starch-PCL, Starch-PBS, Starch-PHB, Blends of PHBV and PPC, Blends of Poly (aspartic acid-co-lactide) (PAL) and PLLA, PBS, and/or PCL, and copolymers, block-copolymers, dendrimers, or mixtures thereof. In one embodiment, the matrix comprises a copolymer. In one embodiment, the matrix comprises a block copolymer. In one embodiment, the matrix comprises poly(lactic-co-glycolic acid) (PLGA). In one embodiment, the matrix is non-toxic. In one embodiment, the matrix is biocompatible. In one embodiment, the matrix is hydrophilic. In one embodiment, the matrix comprises water. In one embodiment, the matrix is hydrophobic. In one embodiment, the matrix comprises a lipid.

In some embodiments, matrix 110 comprises a non-biodegradable matrix. In some embodiments, matrix 110 comprises a semi-biodegradable matrix. In one embodiment, the non-biodegradable matrix comprises a non-biodegradable polymer. In one embodiment, the semi-biodegradable matrix comprises a semi-biodegradable polymer, or a mixture, copolymer, or block copolymer of biodegradable and non-biodegradable polymers. Exemplary non-biodegradable polymers include, but are not limited to, glass, polydimethylsiloxane (PDMS), polyurethane, polymethylmethacrylate (PMMA), polystyrene, cellophane, polyethylene, Polytetrafluoroethylene, poly(propylene), poly(vinyl chloride) (PVC), poly(hydroxyethyl methacrylate) (pHEMA), poly (ethylene terephthalate), polyether ether ketone (PEEK), polyether sulfone (PES), Nylon 6.6, high density polyethylene (HDPE), ultra high molecular weight polyethylene (UHMWPE), Highly crosslinked polyethylene (HXPE), Poly(ethylene glycol) (PEG), expanded PTFE (ePTFE), Poly(vinylpyrrolidone) (PVP), Poly(styrene-b-isobutylene-b-styrene) (SIBS), and combinations, mixtures, copolymers, and/or block copolymers thereof.

In some embodiments of the invention, the biodegradable matrix further comprises at least one compound which is a chemotherapeutic agent, a radionuclide, a ligand (such as, for example, a radioligand), a radionuclide chelator, and MRI contrast agent, or a boron-10-containing compound. In some embodiments, degradation of the biodegradable matrix causes release of the compound. In some embodiments, the biodegradable matrix comprises multiple compounds.

In one embodiment, the micro-beads are substantially spherical. In one embodiment, the micro-beads are irregularly shaped. In one embodiment, the micro-beads are cylindrical. In one embodiment, the diameter of the micro-beads, or average diameter if non-spherical, is less than about 1000 μm. In one embodiment, the diameter of the micro-beads is between about 1000 μm and about 30 μm. In one embodiment, the diameter of the micro-beads is about 1000 μm. In one embodiment, the diameter of the micro-beads is about 950 μm. In one embodiment, the diameter of the micro-beads is about 900 μm. In one embodiment, the diameter of the micro-beads is about 850 μm. In one embodiment, the diameter of the micro-beads is about 800 μm. In one embodiment, the diameter of the micro-beads is about 750 μm. In one embodiment, the diameter of the micro-beads is about 700 μm. In one embodiment, the diameter of the micro-beads is about 650 μm. In one embodiment, the diameter of the micro-beads is about 600 μm. In one embodiment, the diameter of the micro-beads is about 550 μm. In one embodiment, the diameter of the micro-beads is about 500 μm. In one embodiment, the diameter of the micro-beads is about 450 μm. In one embodiment, the diameter of the micro-beads is about 400 μm. In one embodiment, the diameter of the micro-beads is about 350 μm. In one embodiment, the diameter of the micro-beads is about 300 μm. In one embodiment, the diameter of the micro-beads is about 250 μm. In one embodiment, the diameter of the micro-beads is about 200 μm. In one embodiment, the diameter of the micro-beads is about 150 μm. In one embodiment, the diameter of the micro-beads is about 100 μm. In one embodiment, the diameter of the micro-beads is about 90 μm. In one embodiment, the diameter of the micro-beads is about 80 μm. In one embodiment, the diameter of the micro-beads is about 70 μm. In one embodiment, the diameter of the micro-beads is about 60 μm. In one embodiment, the diameter of the micro-beads is about 50 μm. In one embodiment, the diameter of the micro-beads is about 40 μm. In one embodiment, the diameter of the micro-beads is about 30 μm.

In one embodiment, the diameter of the micro-beads is between about 20 μm and about 1 μm. In one embodiment, the diameter of the micro-beads is between about 5 μm and about 15 μm. In one embodiment, the diameter of the micro-beads is about 15 μm. In one embodiment, the diameter of the micro-beads is about 14 μm. In one embodiment, the diameter of the micro-beads is about 13 μm. In one embodiment, the diameter of the micro-beads is about 12 μm. In one embodiment, the diameter of the micro-beads is about 11 μm. In one embodiment, the diameter of the micro-beads is about 10 μm. In one embodiment, the diameter of the micro-beads is about 9 μm. In one embodiment, the diameter of the micro-beads is about 8 μm. In one embodiment, the diameter of the micro-beads is about 7 μm. In one embodiment, the diameter of the micro-beads is about 6 μm. In one embodiment, the diameter of the micro-beads is about 5 μm.

The micro-beads of the invention comprise a plurality of nanospheres, nanoparticles, or nano-beads. The nano-beads may have a uniform shape, such as a sphere, or may have irregular shapes such as nanoshards. In one embodiment, the nano-beads are completely solid. In one embodiment, the nano-beads are hollow. In one embodiment, the nano-beads are substantially spherical. In one embodiments, the nano-beads comprise metal or gold nanoparticles. In one embodiment, the nano-beads comprise a physiologically or pharmaceutically acceptable material, for example glass or gold, or a biodegradable, semi-biodegradable, or non-degradable polymer. Exemplary polymers include, but are not limited to, poly(methyl methacrylate) (PMMA), polystyrene, carboxymethyl chitosan (CCN), or carboxymethyl cellulose (CMC). In one embodiment, the polymer is non-toxic, biocompatible, and/or hydrophilic.

In one embodiment, the nano-beads comprise metallic nanobeads. In one embodiment, the nano-beads comprise metallic nanoparticles. In one embodiment, the nano-beads comprise gold nanoparticles.

In one embodiment, the nano-beads comprise PLGA. In one embodiment, the ratio of lactide to glycolide monomers can be selected to control the degradation rate. In one embodiment, increasing the proportion of glycolide in the copolymer increases the degradation rate. In one embodiment, decreasing the proportion of glycolide in the copolymer decreases the degradation rate. Suitable ratios of lactide to glycolide are easily determined by one of skill in the art.

In some embodiments, the nano-beads comprise biodegradable polymer discussed herein. In some embodiments, the nano-beads comprise a semi-biodegradable or non-biodegradable polymer. Exemplary non-biodegradable polymers include, but are not limited to, polydimethylsiloxane (PDMS), polyurethane, polymethylmethacrylate (PMMA), cellophane, polyethylene, Polytetrafluoroethylene, poly (propylene), poly(vinyl chloride) (PVC), poly(hydroxyethyl methacrylate) (pHEMA), poly(ethylene terephthalate), polyether ether ketone (PEEK), polyether sulfone (PES), Nylon 6.6, high density polyethylene (HDPE), ultra high molecular weight polyethylene (UHMWPE), Highly cross-linked polyethylene (HXPE). Poly(ethylene glycol) (PEG), expanded PTFE (ePTFE), Poly(vinylpyrrolidone) (PVP), Poly(styrene-b-isobutylene-b-styrene) (SIBS), and combinations, mixtures, copolymers, and/or block copolymers thereof.

In one embodiment, the nano-beads are of substantially similar diameter, or average diameter if non-spherical. In one embodiment, the nano-beads are of various diameters. In one embodiment, the nano-bead diameters fall within a gaussian distribution. In one embodiment, the average diameter of the nano-beads is greater than about 1 nm. In one embodiment, the average diameter of the nano-beads is less than about 500 nm. In one embodiment, the average diameter of the nano-beads is less than about 450 nm. In one embodiment, the average diameter of the nano-beads is less than about 400 nm. In one embodiment, the average diameter of the nano-beads is less than about 350 nm. In one embodiment, the average diameter of the nano-beads is less than about 300 nm. In one embodiment, the average diameter of the nano-beads is less than about 250 nm. In one embodiment, the average diameter of the nano-beads is less than about 200 nm. In one embodiment, the average diameter of the nano-beads is less than about 150 nm. In one embodiment, the average diameter of the nano-beads is less than about 100 nm. In one embodiment, the average diameter of the nano-beads is less than about 90 nm. In one embodiment, the average diameter of the nano-beads is less than about 80 nm. In one embodiment, the average diameter of the nano-beads is less than about 70 nm. In one embodiment, the average diameter of the nano-beads is less than about 60 nm. In one embodiment, the average diameter of the nano-beads is less than about 50 nm. In one embodiment, the average diameter of the nano-beads is less than about 40 nm. In one embodiment, the average diameter of the nano-beads is less than about 30 nm. In one embodiment, the average diameter of the nano-beads is less than about 20 nm. In one embodiment, the average diameter of the nano-beads is greater than about 10 nm.

In some embodiments of the invention, the nano-beads are sub-microbeads, such as is shown in FIG. 2. In one embodiment, the sub-microbeads are only slightly smaller than the micro-beads. In one embodiment, the sub-micro-beads are non-functionalized. In other embodiments, the sub-microbeads comprise any functional elements 130 or 140, or any functional element discussed herein. In one embodiment, the sub-microbeads are less than 1000 μm in diameter. In one embodiment, the sub-microbeads are less than 950 μm in diameter. In one embodiment, the sub-microbeads are less than 900 μm in diameter. In one embodiment, the sub-microbeads are less than 850 μm in diameter. In one embodiment, the sub-microbeads are less than 800 μm in diameter. In one embodiment, the sub-microbeads are less than 750 μm in diameter. In one embodiment, the sub-microbeads are less than 700 μm in diameter. In one embodiment, the sub-microbeads are less than 650 μm in diameter. In one embodiment, the sub-microbeads are less than 600 μm in diameter. In one embodiment, the sub-microbeads are less than 550 μm in diameter. In one embodiment, the sub-microbeads are less than 500 μm in diameter. In one embodiment, the sub-microbeads are less than 450 μm in diameter. In one embodiment, the sub-microbeads are less than 400 μm in diameter. In one embodiment, the sub-microbeads are less than 350 μm in diameter. In one embodiment, the sub-microbeads are less than 300 μm in diameter. In one embodiment, the sub-microbeads are less than 250 μm in diameter. In one embodiment, the sub-microbeads are less than 200 μm in diameter. In one embodiment, the sub-microbeads are less than 150 μm in diameter. In one embodiment, the sub-microbeads are less than 100 μm in diameter. In one embodiment, the sub-microbeads are less than 90 μm in diameter. In one embodiment, the sub-microbeads are less than 80 μm in diameter. In one embodiment, the sub-microbeads are less than 70 μm in diameter. In one embodiment, the sub-microbeads are less than 60 μm in diameter. In one embodiment, the sub-microbeads are less than 50 μm in diameter. In one embodiment, the sub-microbeads are less than 40 μm in diameter. In one embodiment, the sub-microbeads are less than 30 μm in diameter. In one embodiment, the sub-microbeads are less than 20 μm in diameter. In one embodiment, the sub-microbeads are less than 10 μm in diameter.

In some embodiments, the micro-bead of the present invention comprises coating layer 250. In one embodiment, the coating layer comprises a biodegradable polymer. In one embodiment, the dissolution period of the coating layer is between about 1 day and about 3 days.

In some embodiments, the micro-bead of the present invention comprises separation layers 230 and/or 240. In one embodiment, the separation layers comprise a lipid or a mixture of lipids suitable for intravascular administration. In one embodiment, separation layers 230 and 240 comprise lipids used in total parenteral nutrition (TPN). Exemplary lipids, or mixtures of lipids, include, but are not limited to, phospholipids, fatty acids, fatty alcohols, neutral fats, phosphatides, oils, glycolipids, aliphatic alcohols, waxes, terpenes and steroids. The phrase semi-synthetic (or modified natural) denotes a natural compound that has been chemically modified in some fashion.

Examples of phospholipids include native and/or synthetic phospholipids. Phospholipids that can be used include, but are not limited to, phosphatidylcholines (saturated and unsaturated), phosphatidylglycerols, phosphatidylethanolamines, phosphatidylserines, phosphatidic acids, phosphatidylinositols, sphingolipids, diacylglycerides, cardiolipin, ceramides, cerebrosides and the like. Exemplary phospholipids include, but are not limited to, dipalmitoyl phosphatidylcholine (DPPC), dilauryl phosphatidylcholine (DLPC) (C12:0), dimyristoyl phosphatidylcholine (DMPC) (C14:0), distearoyl phosphatidylcholine (DSPC), diphytanoyl phosphatidylcholine, nonadecanoyl phosphatidylcholine, arachidoyl phosphatidylcholine, dioleoyl phosphatidylcholine (DOPC) (C18:1), dipalmitoleoyl phosphatidylcholine (C16:1), linoleoyl phosphatidylcholine (C18:2), myristoyl palmitoyl phosphatidylcholine (MPPC), steroyl myristoyl phosphatidylcholine (SMPC), steroyl palmitoyl phosphatidylcholine (SPPC), palmitoyloleoyl phosphatidylcholine (POPC), palmitoyl palmitooleoyl phosphatidylcholine (PPoPC), dipalmitoyl phosphatidylethanolamine (DPPE), palmitoyloleoyl phosphatidylethanolamine (POPE), dioleoylphosphatidylethanolamine (DOPE), dimyristoyl phosphatidylethanolamine (DMPE), distearoyl phosphatidylethanolamine (DSPE), dioleoyl phosphatidylglycerol (DOPG), palmitoyloleoyl phosphatidylglycerol (POPG), dipalmitoyl phosphatidylglycerol (DPPG), dimyristoyl phosphatidylglycerol (DMPG), distearoyl phosphatidylglycerol (DSPG), dimyristoylphosphatidylserine (DMPS), distearoylphosphatidylserine (DSPS), palmitoyloleoyl phosphatidylserine (POPS), soybean lecithin, egg yolk lecithin, sphingomyelin, phosphatidylinositols, diphosphatidylglycerol, phosphatidylethanolamine, phosphatidic acids, and egg phosphatidylcholine (EPC).

Examples of fatty acids and fatty alcohols include, but are not limited to, sterols, palmitic acid, cetyl alcohol, lauric acid, myristic acid, stearic acid, phytanic acid, dipamlitic acid, and the like. Exemplary fatty acids include palmitic acid. Examples of fatty acid esters include, but are not limited to, methyl palmitate, ethyl palmitate, isopropyl palmitate, cholesteryl palmitate, palmityl palmitate sodium palmitate, potassium palmitate, tripalmitin, and the like.

In one embodiment, separation layers 230 and/or 240 comprise a commercially available lipid emulsion. Exemplary lipid emulsions include, but are not limited to, Intralipid® and Structolipid® (Fresenius, Germany), Liposyn®, Liposyn II® and Liposyn HI® (Hospira Inc.), Travamulsion® (Baxter), Soyacal® (Alpha Therapeutics) and Lipofundin® (B. Braun Medical Inc.). These lipid emulsions typically comprise a vegetable oil, such as soybean oil or safflower oil, an emulsifying agent, such as egg phospholipids, glycerol, and water. Omegaven® (Fresenius, Germany) is a 10% fish oil emulsion with a high percentage of omega-3 fatty acids, eicosapentaenoic acid (EPA) and docosapentaenoic acid (DHA).

Referring again to FIG. 1, in one aspect, the invention relates to an embolization micro-bead comprising a plurality of nano-beads 120, optionally including a variety of functional elements 130, such as ligands, including radioligands, radionuclide chelators, or chemotherapeutic agents. Other functional elements 140 can be included, for example cell penetrating peptides. In one embodiment, the nano-beads comprise radionuclides, either embedded in the mass of the nano-beads, or chelated by radionuclide chelators. As readily apparent, the functional elements of the nano-beads can be embedded in the mass of the bead, or appended on its surface. Any number of methods known in the art can be used to append functional elements 130 and 140 to the surface of nano-beads, including, but not limited to, chemical conjugation through peptide, ester, ether, or click chemistry linking (Biao et al., 2015, Chem Commun (Camb), 51(2) 273-275, Pandori et al., 2005, Virology, 299(2) 204-212). In some embodiments, the nano-beads are non-functionalized.

In some embodiments, the nano-beads comprise a label such as used in medical diagnosis. In one embodiment, the label is selected from the group consisting of an affinity label molecule, a photoaffinity label, a dye, a chromophore, a fluorescent molecule, a phosphorescent molecule, a chemiluminescent molecule, an energy transfer agent, a photocrosslinker molecule, a redox-active molecule, an isotopic label molecule, a spin label molecule, a metal chelator, a metal-comprising moiety, a contrast agent molecule, a MRI contrast agent, a PET contrast agent, a radiopaque contrast agent, a polypeptide, a carbohydrate, a polynucleotide, a peptide nucleic acid, a fatty acid, a lipid, biotin, a biotin analogue, a polymer, and any combination thereof.

In one embodiment, the nano-beads comprise an MRI contrast agent. In one embodiment, the MRI contrast agent is a gadolinium (III) contrast agent. Exemplary MRI contrast agents include, but are not limited to, Clariscan®, Feridex®I.V., gadobenate, gadobutrol, gadocoletic acid, gadodiamide, gadofosveset, gadomelitol, gadomer 17, gadopentetate, gadopentetic acid dimeglumine, gadoterate, gadoteridol, gadoverset amide, gadoxetate, gadoxetate, Lumirem®, Perflubron, Resovist®, Sinerem®, and the like.

Various radionuclides can be included in the nano-beads, such as for example a emitters, beta emitters, gamma emitters, or positron emitters. Radionuclide therapy has been used to treat malignant solid tumors and uses a radioactive atom which serves as a radiation source to destroy cancer cells. Often times pharmaceutical drugs that are used to treat cancer are made with radionuclides. These drugs are referred to as radiopharmaceuticals. Radionuclide therapy is particular effective when targeting cancer cells because cancer cells absorb radioactive substances more readily than normal cells. Radioisotopes can differ depending on the type of cancer a patient may have.

In one embodiment, the nano-bead comprises a combination of radionuclides such as alpha emitting radiation and short-range beta emitting radiation. In some embodiments, the radionuclides can be radioisotopes such as astatine-211, actinium-225, bismuth-213, cesium-131, cesium-137, chromium-51, cobalt-60, dysprosium-165, erbium-169, holmium-166, iodine-125, iodine-131, iridium-192, iron-59, lead-212, bismuth-212, polonium-212, lutetium-177, molybdenum-99, palladium-103, phosphorus-32, potassium-42, radium-223, rhenium-186, rhenium-188, samarium-153, selenium-75, sodium-24, strontium-89, technetium-99, xenon-133, ytterbium-169, ytterbium-177, or yttrium-90. In other embodiments, the radionuclides can be radioisotopes such as carbon-11, carbon-14, nitrogen-13, oxygen-15, fluorine-18, cobalt-57, copper-64, copper-67, gallium-67, gallium-68, germanium-68, indium-111, iodine-123, iodine-124, krypton-81, rubidium-81, rubidium-82, strontium-82, or thallium-201.

In some embodiments, the nano-beads include radionuclide chelators, either embedded in the nano-beads, or appended to the surface of the nano-beads. In some embodiments, the nano-beads include ligands, either embedded in the nano-beads, or appended to the surface of the nano-beads. Ligands or radionuclide chelators have been used for labeling oligomers such as RNA or DNA with metallic radionuclides such as Rhenium-188 ($^{188}$Re) (Liu, et al., 2010, Materials, 3, 3204-3217). Ligands have also been used to characterize the binding of a drug to its receptor target, proving information on the mode of interaction as well as its affinity. Ligands or radionuclide chelators have also been used in imaging techniques such as position emission tomography (PET) or single photon emission computerized tomography (SPECT).

In one embodiment, the radionuclide chelator is selected from the group consisting of acyclic polyaminocarboxylate chelates such as ethylenediamine tetraacetic acid (EDTA) Me-EDTA, CHX-EDTA, DTPA, and CHX-DTPA; triethylenetetramine (TETA) and TETA derivatives including PEPA, 2C-TETA, 6C-TETA, BF-PEPA and BF-HEHA; 1,4, 7-triazacyclononane-1,4,7-trisacetic acid (NOTA) and NOTA derivatives including C-NOTA, N-NOTA, NODASA DTPA, and TCMC; diethylenetriamine pentaacetic acid (DTPA) and DPTA derivatives including a-DTPA, carb-DTPA, ca-DTPA, ibca-DTPA, 1B4M-DTPA, lys-DTPA, vinyl DTPA, glu-DTPA, CHX-A" DTPA; 1,4,7,10-tetraaza-cyclododecane-1,4,7,10-tetraacetic acid (DOTA) and DOTA derivatives including C-DOTA, PA-DOTA, DODASA, and lys-DOTA; and ferrioxamine and related chelators of biological origin.

In one embodiment, the ligand is selected from the group consisting of an antibody, an antibody fragment (e.g. scFv and Fab), a peptide, and a small molecule, and the ligand specifically targets or binds a specific target tissue such as cancer. In one embodiment, the ligand is selected from the group consisting of altanserin, setoperone, ketanserin, flumazenil, 3-amino-4-(2-dimethylaminomethylphenylsulfanyl)-benzonitrile DASB), raclopride, Ioflupane, and Altropane.

In one embodiment, the ligand comprises a radioligand. Exemplary radioligands include, but are not limited to, $^{11}$C-Labeled radioligands such as [$^{11}$C]PIB, [$^{11}$C](R)-PK 11195, [$^{11}$C]PBR28, [$^{11}$C]DAA1106, [$^{11}$C]DPA-713, [$^{11}$C]MP4A, [$^{11}$C]VOR, [$^{11}$C]CURB, [$^{11}$C]Harmine, [$^{11}$C]Clorgyline, [$^{11}$C]Befloxatone, [$^{11}$C]Deprenyl-d2, [$^{11}$C](R)-Rolipram, [$^{11}$C]IMA107, [$^{11}$C]MP-10, [$^{11}$C]Lu AE92686, [$^{11}$C]SCH442416, [$^{11}$C]Flumazenil, [$^{11}$C]Ro15 4513, [$^{11}$C]MePPEP, [$^{11}$C]OMAR, [$^{11}$C]SD5024, [$^{11}$C]NNC 112, [$^{11}$C]SCH 23390, [$^{11}$C]Raclopride, [$^{11}$C]FLB 457, [$^{11}$C]MNPA (agonist), [$^{11}$C](+)PHNO (agonist), [$^{11}$C]NPA (agonist), [$^{11}$C]Doxepin, [$^{11}$C]GSK189254, [$^{11}$C]GR 103545, [carbonyl-$^{11}$C]WAY, [carbonyl-$^{11}$C]DWAY, [$^{11}$C]CUMI (antagonist), [$^{11}$C]AZ10419369, [$^{11}$C]P943, [$^{11}$C]MDL 1000907, [$^{11}$C]SB-207145, [$^{11}$C]GSK-215083, [$^{11}$C]FIMX, [$^{11}$C]SP 203, [$^{11}$C]ABP688, [$^{11}$C]NOP-1A, [$^{11}$C]Methylnaltrindole, [$^{11}$C]Diprenorphine, [$^{11}$C]Carfentanil (agonist), [$^{11}$C]SA4503, [$^{11}$C]PE2I, [$^{11}$C]Methylphenidate, [$^{11}$C]CFpyPB, [$^{11}$C]GSK 931145, [$^{11}$C]RO5013853, [$^{11}$C]MeNER-d2, [$^{11}$C]3-amino-4-(2-dimethylaminomethylphenylsulfanyl)-benzonitrile ([$^{11}$C]DASB), [$^{11}$C]MADAM, [$^{11}$C]AFM, [$^{11}$C]HOHMADAM, [$^{11}$C]DTBZ, and [$^{11}$C]MTBZ; $^{18}$F-Labeled radioligands and/or PET contrast agents such as [$^{18}$F]Flutemetamol, [$^{18}$F]Florbetapir([$^{18}$F]AV-45), [$^{18}$F]AZD 4694, [$^{18}$F]FBM, [$^{18}$F]FDDNP, [$^{18}$F]-SMIBR-W372 ([F-18]W372), [$^{18}$F]Florbetaben, [$^{18}$F]MK3328, [$^{18}$F]BF-227, [$^{18}$F]THK523, [$^{18}$F]FBR, [$^{18}$F]FEPPA, [$^{18}$F]PBR111, [$^{18}$F]MNI659, [$^{18}$F]CPFPX, [$^{18}$F]Flumazenil, [$^{18}$F]FEM-MEP-d2, [$^{18}$F]MK-9470, [$^{18}$F]Fallypride, [$^{18}$F]FMH3, [$^{18}$F]FCWAY, [$^{18}$F]MefWAY, [$^{18}$F]MPPF, [$^{18}$F]Altanserin, [$^{18}$F]Setoperone, [$^{18}$F]ketanserin, [$^{18}$F]Altanserin-d2, [$^{18}$F]FITM, [$^{18}$F]SP 203, [$^{18}$F]F-FPEB, 2-[$^{18}$F]F-A-85380 (2-[$^{18}$F]FA), 6-[$^{18}$F]FA, [$^{18}$F]Nifene (agonist), [$^{18}$F]AZAN, [$^{11}$C]CHIBA-1001, [$^{18}$F]ASEM, [$^{18}$F]SPA-RQ, [$^{18}$F]MK-0999 ([$^{18}$F]FE-SPA-RQ), [$^{18}$F]GE-179, [$^{18}$F]Fluoroethyl-diprenorphine, [$^{18}$F]FP-CIT, [$^{18}$F]FE-PE2I, [$^{18}$F]FECNT, [$^{18}$F]CFPyPB, [$^{18}$F]FMeNER-d2, [$^{18}$F]florbenazine, [$^{18}$F]AV-133, and [$^{18}$F]FP-DTBZ; and $^{123}$I-containing radioligands such as [$^{123}$I]IMPY, [$^{123}$I]CLINDE, [$^{123}$I]IBVM, [$^{123}$I]MNI420, [$^{123}$I]IBZM, [$^{123}$I]Epidepride, [$^{123}$I]5IA, [$^{123}$I]Ioflupane (FP-CIT; DATSCAN), [$^{123}$I]CIT (Dopascan), [$^{123}$I]Altropane, [$^{123}$I]PE2I, [$^{123}$I]INER, [$^{123}$I]CIT, [$^{123}$I]metaiodobenzylguanidine, and [$^{123}$I]mZIENT.

In some embodiments, the nano-beads include one or more chemotherapeutic agents, either embedded in the nano-beads, or appended to the surface of the nano-beads. In one embodiment, the chemotherapeutic agent is slowly released from the nano-beads. In one embodiment, the chemotherapeutic agent is bound to the nano-beads, such as via a covalent bond or non-covalent interaction.

In one embodiment, the chemotherapeutic agent is dissociable. In one embodiment, the dissociable bond is stable in extracellular environment but dissociated in the intracellular environment (e.g. Cys-Cys linker or Cystamine linker). In one embodiment, the dissociable bond comprises an enzymatically cleaved moiety, such as an ester. In one embodiment, the dissociable bond comprises an enzymatically cleaved polypeptide.

Exemplary chemotherapeutic agents include, but are not limited to, cytotoxic agents (e.g., 5-fluorouracil, cisplatin, carboplatin, methotrexate, daunorubicin, doxorubicin, vincristine, vinblastine, oxorubicin, carmustine (BCNU), lomustine (CCNU), cytarabine USP, cyclophosphamide, estramucine phosphate sodium, altretamine, hydroxyurea, ifosfamide, procarbazine, mitomycin, busulfan, cyclophosphamide, mitoxantrone, carboplatin, cisplatin, interferon alfa-2a recombinant, paclitaxel, teniposide, and streptozoci), cytotoxic alkylating agents (e.g., busulfan, chlorambucil, cyclophosphamide, melphalan, or ethylesulfonic acid), alkylating agents (e.g., asaley, AZQ, BCNU, busulfan, bisulphan, carboxyphthalatoplatinum, CBDCA, CCNU, CHIP, chlorambucil, chlorozotocin, cis-platinum, clomesone, cyanomorpholinodoxorubicin, cyclodisone, cyclophosphamide, dianhydrogalactitol, fluorodopan, hepsulfam, hycanthone, iphosphamide, melphalan, methyl CCNU, mitomycin C, mitozolamide, nitrogen mustard, PCNU, piperazine, piperazinedione, pipobroman, porfiromycin, spirohydantoin mustard, streptozotocin, teroxirone, tetraplatin, thiotepa, triethylenemelamine, uracil nitrogen mustard, and Yoshi-864), antimitotic agents (e.g., allocolchicine, Halichondrin M, colchicine, colchicine derivatives, dolastatin 10, maytansine, rhizoxin, paclitaxel derivatives, paclitaxel, thiocolchicine, trityl cysteine, vinblastine sulfate, and vincristine sulfate), plant alkaloids (e.g., actinomycin D, bleomycin, L-asparaginase, idarubicin, vinblastine sulfate, vincristine sulfate, mitramycin, mitomycin, daunorubicin, VP-16-213, VM-26, navelbine and taxotere), biologicals (e.g., alpha interferon, BCG, G-CSF, GM-CSF, and interleukin-2), topoisomerase I inhibitors (e.g., camptothecin, camptothecin derivatives, and morpholinodoxorubicin), topoisomerase II inhibitors (e.g., mitoxantron, amonafide, m-AMSA, anthrapyrazole derivatives, pyrazoloacridine, bisantrene HCL, daunorubicin, deoxydoxorubicin, menogaril, N,N-dibenzyl daunomycin, oxanthrazole, rubidazone, VM-26 and VP-16), and synthetics (e.g., hydroxyurea, procarbazine, o,p'-DDD, dacarbazine, CCNU, BCNU, cis-diammin-edichloroplatimun, mitoxantrone, CBDCA, levamisole, hexamethylmelamine, all-trans retinoic acid, gliadel and porfimer sodium).

In one embodiment, the chemotherapeutic agent is an antiproliferative agent. Antiproliferative agents are compounds that decrease the proliferation of cells. Antiproliferative agents include alkylating agents, antimetabolites, enzymes, biological response modifiers, miscellaneous agents, hormones and antagonists, androgen inhibitors (e.g., flutamide and leuprolide acetate), antiestrogens (e.g., tamoxifen citrate and analogs thereof, toremifene, droloxifene and roloxifene), Additional examples of specific antiproliferative agents include, but are not limited to levamisole, gallium nitrate, granisetron, sargramostim strontium-89 chloride, filgrastim, pilocarpine, dexrazoxane, and ondansetron.

In one embodiment, the chemotherapeutic agent is a cytotoxic/antineoplastic agent or an anti-angiogenic agent. Cytotoxic/anti-neoplastic agents are defined as agents which attack and kill cancer cells. Some cytotoxic/anti-neoplastic agents are alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents are antimetabolites for tumor cells, e.g., cytosine arabinoside, fluorouracil, methotrexate, mercaptopuirine, azathioprime, and procarbazine. Other cytotoxic/anti-neoplastic agents are antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents are mitotic inhibitors (vinca alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents are well known to those of skill in the art. Suitable anti-angiogenic agents for use in the methods and compositions of the present disclosure include anti-VEGF antibodies, including humanized and chimeric antibodies, anti-VEGF aptamers and antisense oligonucleotides. Other known inhibitors of angiogenesis include angiostatin, endostatin, interferons, interleukin 1 (including alpha and beta) interleukin 12, retinoic acid, and tissue inhibitors of metalloproteinase-1 and -2. (TIMP-1 and -2). Small molecules, including topoisomerases such as razoxane, a topoisomerase II inhibitor with anti-angiogenic activity, can also be used.

In one embodiment, the chemotherapeutic agent is selected from the group consisting of acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; bortezomib; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-Ia; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflomithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In some embodiments, the nano-beads include one or more color pigments. In some embodiments the color pigment is a biocompatible colorant, which are generally known to those of skill in the art. Exemplary color pigments include, but are not limited to, the FD&C dyes, D&C dyes, and others as described in FDA 21 CFR § 73 and 74 that FDA has permitted to be used in approved medical devices. Additional color pigments include natural color pigments. Exemplary color pigments include, but are not limited to, [phthalocyaninato(2-)] copper, 1,4-bis[(2-hydroxyethyl)amino]-9,10-anthracenedione bis(2-methyl-2-propenoic)ester copolymers, 1,4-bis[(2-methylphenyl)amino]-9,10-anthracenedione, 1,4-bis[4-(2-methacryloxyethyl)phenylamino]anthraquinone copolymers, 16,17-dimethoxydinaphtho[1,2,3-cd:3',2',1'-lm] perylene-5,10-dione, 16,23-dihydrodinaphtho[2,3-a: 2',3'-i]naphth[2',3':6,7]indolo[2,3-c] carbazole-5,10,15,17,22,24-hexone, 2-[[2,5-diethoxy-4-[(4-methylphenyl)thiol]phenyl]azo]-1,3,5-benzenetriol, 4-[(2,4-dimethylphenyl)azo]-2,4-dihydro-5-methyl-2-phenyl-3H-pyrazol-3-one, 6-ethoxy-2-(6-ethoxy-3-oxobenzo[b]thien-2(3H)-ylidene) benzo[b]thiophen-3 (2H)-one, 7,16-dichloro-6,15-dihydro-5,9,14,18-anthrazinetetrone, alumina (dried aluminum hydroxide), aluminum powder, annatto extract, annatto, astaxanthin dimethyldisuccinate, bismuth citrate, bismuth oxychloride, bronze powder, C.I. vat orange 1, calcium carbonate, canthaxanthin, caramel, carbazole violet, carmine, carrot oil, chlorophyllin-copper complex, oil soluble, chromium hydroxide green, chromium hydroxide green, chromium oxide greens, chromium-cobalt-aluminum oxide, citrus red no. 2, cochineal extract, carmine, copper powder, corn endosperm oil, D&C black no. 2, D&C black no. 3, D&C black no. 4, D&C blue no. 4, D&C blue no. 6, D&C blue no. 9, D&C brown no. 1, D&C green no. 5, D&C green no. 6, D&C green no. 8, D&C orange no. 10, D&C orange no. 11, D&C orange no. 4, D&C orange no. 5, D&C red no. 17, D&C red no. 21, D&C red no. 22, D&C red no. 27, D&C red no. 28, D&C red no. 30, D&C red no. 31, D&C red no. 33, D&C red no. 34, D&C red no. 36, D&C red no. 39, D&C red no. 6, D&C red no. 7, D&C violet no. 2, D&C yellow no. 10, D&C yellow no. 11, D&C yellow no. 11, D&C yellow no. 7, D&C yellow no. 8, D&C yellow no. 8, dehydrated beets (beet powder), dihydroxyacetone, disodium 1-amino-4-[[4-[(2-bromo-1-oxoallyl)amino]-2-sulfonatophenyl]amino]-9,10-dihydro-9,10-dioxoanthracene-2-sulfonate, disodium EDTA-copper, dried algae meal, FD&C blue no. 1, FD&C blue no. 2, FD&C green no. 3, FD&C red no. 3, FD&C red no. 4, FD&C red no. 40, FD&C yellow no. 5, FD&C yellow no. 6, ferric ammonium citrate, Ferric ammonium ferrocyanide, Ferric ferrocyanide, Ferrous gluconate, Ferrous lactate, Fruit juice, Grape color extract, Grape skin extract (enocianina), Guaiazulene, Guanine, Haematococcus algae meal, Henna, Iron oxides, Lead acetate, Logwood extract, Luminescent zinc sulfide, Manganese violet, Mica, Mica-based pearlescent pigments, N,N'-(9,10-dihydro-9,10-dioxo-1,5-anthracenediyl) bisbenzamide, orange b, paprika oleoresin, paprika, paracoccus pigment, phaffia yeast, phthalocyanine green, poly(hydroxyethyl methacrylate)-dye copolymers, potassium sodium copper chloropyhllin (chlorophyllin-copper complex), pyrogallol, pyrophyllite, pyrophyllite, riboflavin, saffron, silver, sodium copper chlorophyllin, soy leghemoglobin, spirulina extract, synthetic iron oxide, tagetes (aztec marigold) meal and extract, talc, titanium dioxide, toasted partially defatted cooked cottonseed flour, tomato lycopene extract; tomato lycopene concentrate, turmeric oleoresin, turmeric, ultramarine blue, ultramarines, vegetable juice, vinyl alcohol/methyl methacrylate-dye reaction products, zinc oxide, β-apo-8'-carotenal, and β-carotene.

In some embodiments, the nano-beads include one or more cell penetrating peptides (CPP). The delivery of therapeutic molecules into cells through cellular uptake has proven to be a difficult task to achieve. The plasma membrane, which protects the cell from its surroundings, regulates what enters and exits the cell, and unless a method of transport is used or the molecule is small (i.e. $CO_2$ or $O_2$) many of these therapeutic molecules are prevented from traversing the plasma membrane. Transportation across the cell membrane can be accomplished using membrane perturbation and viral vectors techniques but can result in low delivery yields and high toxicity. Cell penetrating peptides are a relatively new way of transporting cargo such as therapeutic molecules into a cell. Unlike other peptides, CPPs have the ability to cross the cellular membrane. CPPs can facilitate the transportation of cargo into a cell or an organelle and target intracellular proteins. This cargo can be macromolecules such as therapeutics, or the nano-beads of the present invention.

CPPs can be polycationic, amphipathic, or be comprised of apolar amino acids. CPPs are comprised of short sequences of amino acids which can be between 3-30 amino acids in length. In one embodiment, the CPP is attached to the surface of the nano-bead. In one embodiment, the CPP has a chemotherapeutic agent attached to it. In one embodiment, the cell penetrating peptide can be, but is not limited to, polyarginine, Antennapedia sequences, HIV-1 Tat and related peptides, SynB1, SynB3, PTD-4, PTD-5, penetratin, Antp-3A (Antp mutant), Buforin II, Transportan, MAP (model amphipathic peptide), K-FGF, Ku70, Prion, pVEC, Pep-1, SynB1, Pep-7, FIN-1, BGSC (Bis-Guanidinium-Spermidine-Cholesterol, BGTC (Bis-Guanidinium-Tren-Cholesterol), R9, HSV gH625, VP22, and Xentry. In one embodiment, the cell-penetrating peptide is positively charged. In one embodiment, the cell-penetrating peptide has cell-cell traversing properties, or nuclear localization properties.

Pharmaceutical Composition

For administration of the micro-beads of the invention to a subject, the micro-beads can be suspended in any pharmaceutically acceptable carrier, for example, sterile water or buffered aqueous carriers, such as glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey), the disclosure of which is incorporated by reference as if set forth in its entirety herein. The pharmaceutical compositions comprising the micro-beads of the invention may be prepared, packaged, or sold in the form of a sterile injectable aqueous or oily suspension or solution. This suspension or solution may be formulated according to the known art, and may comprise, in addition to the micro-beads, additional ingredients such as dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides.

Formulations of a pharmaceutical composition suitable for parenteral administration comprise the micro-beads combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

Liquid suspensions may be prepared using conventional methods to achieve suspension of the micro-beads in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, and hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para-hydroxybenzoates, ascorbic acid, and sorbic acid.

Known thickening agents for oily suspensions include, for example, beeswax, hard paraffin, and cetyl alcohol.

A pharmaceutical composition used in the methods of the invention may be prepared, packaged, or sold in bulk, as a single unit dose, or as a plurality of single unit doses. As used herein, a "unit dose" is a discrete amount of the pharmaceutical composition comprising a predetermined amount of micro-beads. The amount of micro-beads is generally equal to the dosage of the micro-beads which would be administered to a subject or a convenient fraction of such a dosage such as, for example, one-half or one-third of such a dosage.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

Neutron Capture Therapy

Neutron capture therapy (NCT) is a powerful and noninvasive method of treating cancer cells. In this two-step treatment, a non-radioactive isotope (capture agent) that has the ability to capture slow neutrons, is injected into the subject. The subject is then irradiated with neutrons from a neutron source, these neutrons are absorbed by the capture agent, which then produce high energy alpha particles, which kill the cancer cells. This described method of treatment is often used with boron-10 and is also known as boron neutron capture therapy (BNCT) (Barth et al., 2012, Radiation Oncology, 7(146): 1-21).

In some embodiments, the nano-beads of the invention include neutron capture agents comprising boron-10 or gadolinium-157. In one embodiment, the neutron capture agents is embedded in the nano-beads. In one embodiment, the neutron capture agents is on the surface of the nano-beads. In one embodiment, the neutron capture agent is in the biodegradable matrix. In one embodiment, the neutron capture agent is selected from the group consisting of boronophenylalanine (BPA), sodium borocaptate (BSH), dodecaborate cluster lipids and cholesterol derivatives, GB10 ($Na_2B_{10}H_{10}$), cholesteryl ester mimics, boronated DNA metallo-intercalators, transferrin-polyethylene glycol (TF-PEG) liposomes, o-closocarboranyl β-lactoside, 1-methyl-o-closocarboranyl-2-hexyl thioporphyrazine, 1-amino-3-boronocyclopentanecarboxylic acid, dodecahydro-closo-dodecaborate clusters, carboranyl nucleosides and thymidine analogues, carboranyl porphyrins such as tetra-(4-nido-carboranylphenyl) porphyrin, boronated EGF and anti-EGFR mAbs, boron-containing nanoparticles, carboranyl porphrazines, boronated cyclic peptides, and boron carbide particles. In one embodiment, the micro-bead containing a plurality of nano-beads comprising atoms of a neutron capture agent delivers at least 10,000 atoms per cell of target tissue or tumor.

Methods of the Invention

In one aspect, the micro-bead acts as a sustained release device, because the biodegradable matrix will slowly degrade releasing the nano-beads into circulation. Therefore, one of the major drawbacks of the state of the art beads is overcome, as the nano-beads including functional elements such as radionuclides, ligands (such as, for example, radioligands), chemotherapeutic agents, cell-penetrating peptides, or neutron capturing atoms, will more homogenously distribute throughout the target tumor. In contrast to the state of the art glass micro-beads which remain lodged at the lowest vascular lumen matching their size, typically on the arterial zones of the tumor, the micro-beads and their embedded nano-beads described herein provide a more homogeneous and deeper distribution of radiation or chemotherapeutic agents to the target tissue, wherein the slow degradation of the micro-beads provides a long term local delivery system. Finally, the micro-beads dissolve in a matter of few weeks, for example between 1 and 90 days, which results in restitution of blood flow to the target organ and facilitated healing.

In therapies such as arterial embolization, chemoembolization and radioembolization, the procedure involves the use of a catheter to inject small particles into the patient to destroy cancer cells. In one embodiment, the micro-bead is administered to the subject by using a catheter. In one embodiment, the micro-bead can be administered by a catheter into the main hepatic artery or branches thereof. Once the micro-bead lodges into the cancerous tumor, degradation of the micro-bead causes the release of the nano-bead coated with a functionalized surface comprising CPPs, radionuclides, radioligands, radionuclide chelators, a dissociable chemotherapeutic agent, or a combination thereof. In one embodiment, CPPs, radionuclide chelators, radioligands, dissociable chemotherapeutic agents are conjugated to the surface of the nano-bead. With the aid of the CPPs, the nano-bead can traverse the cell membrane, resulting in the cancerous cell being destroyed by the chemotherapeutic agent or radiation or a combination thereof.

Various diseases or disorders can be treated by use of the micro-beads and nano-beads of the invention. In one embodiment, the disease or disorder is cancer, such as, but not limited to, Acute Lymphoblastic; Acute Myeloid Leukemia; Adrenocortical Carcinoma; Adrenocortical Carcinoma, Childhood; Appendix Cancer; Basal Cell Carcinoma; Bile Duct Cancer, Extrahepatic; Bladder Cancer; Bone Cancer; Osteosarcoma and Malignant Fibrous Histiocytoma; Brain Stem Glioma, Childhood; Brain Tumor, Adult; Brain Tumor, Brain Stem Glioma, Childhood; Brain Tumor, Central Nervous System Atypical Teratoid/Rhabdoid Tumor, Childhood; Central Nervous System Embryonal Tumors; Cerebellar Astrocytoma; Cerebral Astrocytotna/Malignant Glioma; Craniopharyngioma; Ependymoblastoma; Ependymoma; Medulloblastoma; Medulloepithelioma; Pineal Parenchymal Tumors of intermediate Differentiation; Supratentorial Primitive Neuroectodermal Tumors and Pineoblastoma; Visual Pathway and Hypothalamic Glioma; Brain and Spinal Cord Tumors; Breast Cancer; Bronchial Tumors; Burkitt Lymphoma; Carcinoid Tumor; Carcinoid Tumor, Gastrointestinal; Central Nervous System Atypical Teratoid/Rhabdoid Tumor; Central Nervous System Embryonal Tumors; Central Nervous System Lymphoma; Cerebellar Astrocytoma Cerebral Astrocytoma/Malignant Glioma, Childhood; Cervical Cancer; Chordoma, Childhood; Chronic Lymphocytic Leukemia; Chronic Myelogenous Leukemia; Chronic Myeloproliferative Disorders; Colon Cancer; Colorectal Cancer; Craniopharyngioma; Cutaneous T-Cell Lymphoma; Esophageal Cancer; Ewing Family of Tumors; Extragonadal Germ Cell Tumor; Extrahepatic Bile Duct Cancer; Eye Cancer, intraocular Melanoma; Eye Cancer, Retinoblastoma; Gallbladder Cancer; Gastric (Stomach) Cancer; Gastrointestinal Carcinoid Tumor; Gastrointestinal Stromal Tumor (GIST); Germ Cell Tumor, Extracranial; Germ Cell Tumor, Extragonadal; Germ Cell Tumor, Ovarian; Gestational Trophoblastic Tumor; Glioma; Glioma, Childhood Brain Stem; Glioma, Childhood Cerebral Astrocytoma; Glioma, Childhood Visual Pathway and Hypothalamic; Hairy Cell Leukemia; Head and Neck Cancer; Hepatocellular (Liver) Cancer; Heptatocellular Carcinoma (HCC); Histiocytosis, Langerhans Cell; Hodgkin Lymphoma; Hypopharyngeal Cancer; Hypothalamic and Visual Pathway Glioma; intraocular Melanoma; Islet Cell Tumors; Kidney (Renal Cell) Cancer; Langerhans Cell Histiocytosis; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoma, AIDS-Related; Lymphoma, Burkitt; Lymphoma, Cutaneous T-Cell; Lymphoma, Hodgkin; Lymphoma, Non-Hodgkin; Lymphoma, Primary Central Nervous System; Macroglobulinemia, Waldenstrom; Malignant Fibrous Histiocvtoma of Bone and Osteosarcoma; Medulloblastoma; Melanoma; Melanoma, intraocular (Eye); Merkel Cell Carcinoma; Mesothelioma; Metastatic Squamous Neck Cancer with Occult Primary; Mouth Cancer; Multiple Endocrine Neoplasia Syndrome, (Childhood); Multiple Myeloma/Plasma Cell Neoplasm; Mycosis; Fungoides; Myelodysplastic Syndromes; Myelodysplastic/Myeloproliferative Diseases; Myelogenous Leukemia, Chronic; Myeloid Leukemia, Adult Acute; Myeloid Leukemia, Childhood Acute; Myeloma, Multiple; Myeloproliferative Disorders, Chronic; Nasal Cavity and Paranasal Sinus Cancer; Nasopharyngeal Cancer; Neuroblastoma; Non-Small Cell Lung Cancer; Oral Cancer; Oral Cavity Cancer; Oropharyngeal Cancer; Osteosarcoma and Malignant Fibrous Histiocytoma of Bone; Ovarian Cancer; Ovarian Epithelial Cancer; Ovarian Germ Cell Tumor; Ovarian Low Malignant Potential Tumor; Pancreatic Cancer; Pancreatic Cancer, Islet Cell Tumors; Papillomatosis; Parathyroid Cancer; Penile Cancer; Pharyngeal Cancer; Pheochromocytoma; Pineal Parenchymal Tumors of Intermediate Differentiation; Pineoblastoma and Supratentorial Primitive Neuroectodermal Tumors; Pituitary Tumor; Plasma Celt Neoplasm/Multiple Myeloma; Pleuropulmonary Blastoma; Primary Central Nervous System Lymphoma; Prostate Cancer; Rectal Cancer; Renal Cell (Kidney) Cancer; Renal Cell Carcinoma (RCC); Renal Pelvis and Ureter, Transitional Cell Cancer; Respiratory Tract Carcinoma Involving the NUT Gene on Chromosome 15; Retinoblastoma; Rhabdomyosarcoma; Salivary Gland Cancer; Sarcoma, Ewing Family of Tumors; Sarcoma, Kaposi; Sarcoma, Soft Tissue; Sarcoma, Uterine; Sezary Syndrome; Skin Cancer (Nonmelanoma); Skin Cancer (Melanoma); Skin Carcinoma, Merkel Cell; Small Cell Lung Cancer; Small Intestine Cancer; Soft Tissue Sarcoma; Squamous Cell Carcinoma, Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Throat Cancer; Thymoma and Thymic Carcinoma; Thyroid Cancer; Transitional Cell Cancer of the Renal Pelvis and Ureter; Trophoblastic Tumor, Gestational; Urethral Cancer; Uterine Cancer, Endometrial; Uterine Sarcoma; Vaginal Cancer; Vulvar Cancer; Waldenstrom Macroglobulinemia; Wilms Tumor, and the like.

The methods of treatment of the invention include various administration methods, such as for example parenteral administration. As used herein, "parenteral administration" of a composition of the invention includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intravenous, subcutaneous, intraperitoneal, intramuscular, intrasternal injection, bolus injections, and kidney dialytic infusion techniques. In one embodiment, parenteral administration includes depositing the micro-beads of the invention, or a composition comprising the micro-beads of the present invention, into an artery of a subject.

In one aspect, the invention provides methods comprising the use of theragnostics, or theranostics, further comprising the micro-beads and nano-beads of the invention. Theragnostics, or theranostics, are compounds, formulations and compositions, capable of functioning as both therapeutic agents and diagnostic agents. For example, micro-beads of the invention can deliver a radioisotope or chemotherapeutic agent to a liver tumor, and at the same time provide for the possibility of imaging the tumor, or the radioisotope or chemotherapeutic distribution in the tumor, a cell, tissue, organ, or entire body. Modern approaches to theragnostics, or theranostics, have been described by Xie et al., 2010, Adv Drug Deliv Rev, 62(11):1064-1079, and Pene et al., 2009, Crit Care Med., 37(1 Suppl):S50-8, descriptions incorporated herein in their entirety.

It is to be understood that the figures and descriptions of the present invention have been simplified to illustrate elements that are relevant for a clear understanding of the present invention, while eliminating, for the purpose of clarity, many other elements found in similar technology. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, are not to be construed as limiting in any way the remainder of the disclosure.

Example 1: Imaging and Immunohistochemistry of Micro-Beads

Figure 3:
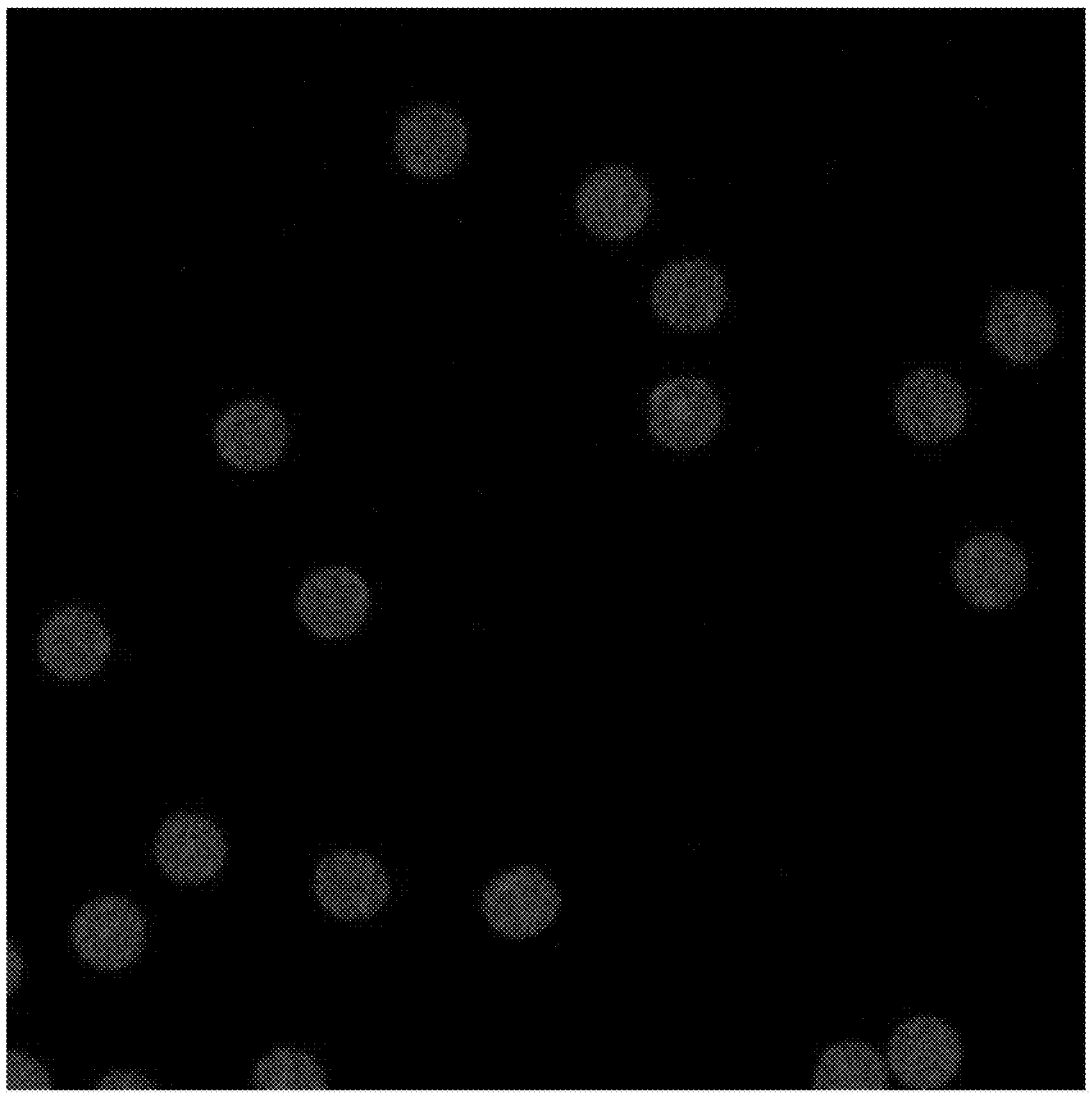
FIG. 3 is a photograph showing red nanoparticles embedded within exemplary 7 μm micro-beads.
Figure 4:
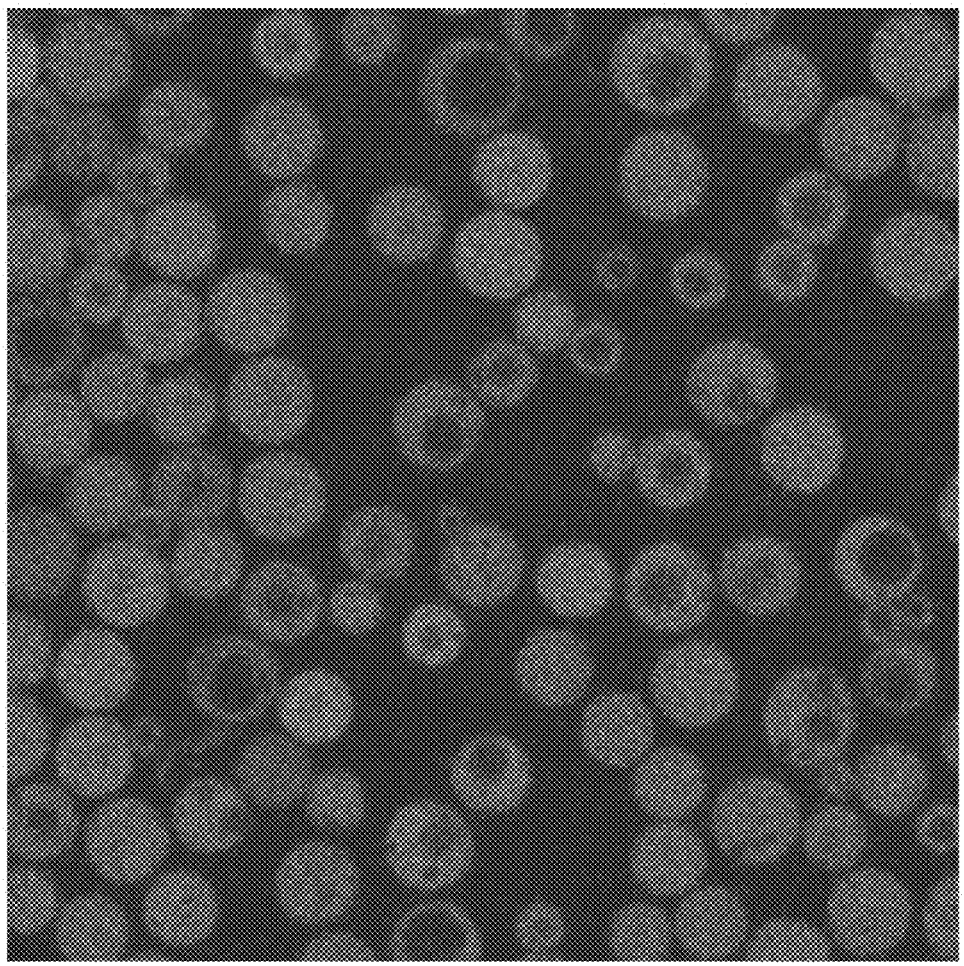
FIG. 4 is a photograph showing red nanoparticles embedded within exemplary 15 μm micro-beads.

Exemplary biodegradable microbeads filled with nano-sized particles measuring 7 μm in diameter (FIG. 3) and 15

µm in diameter (FIG. 4) were generated. The nanosized particles (red particles) are modified to be capable of carrying therapeutic (e.g. radionuclides) and diagnostic (e.g. gadolinium for MRI imaging) moieties.

Figure 5:
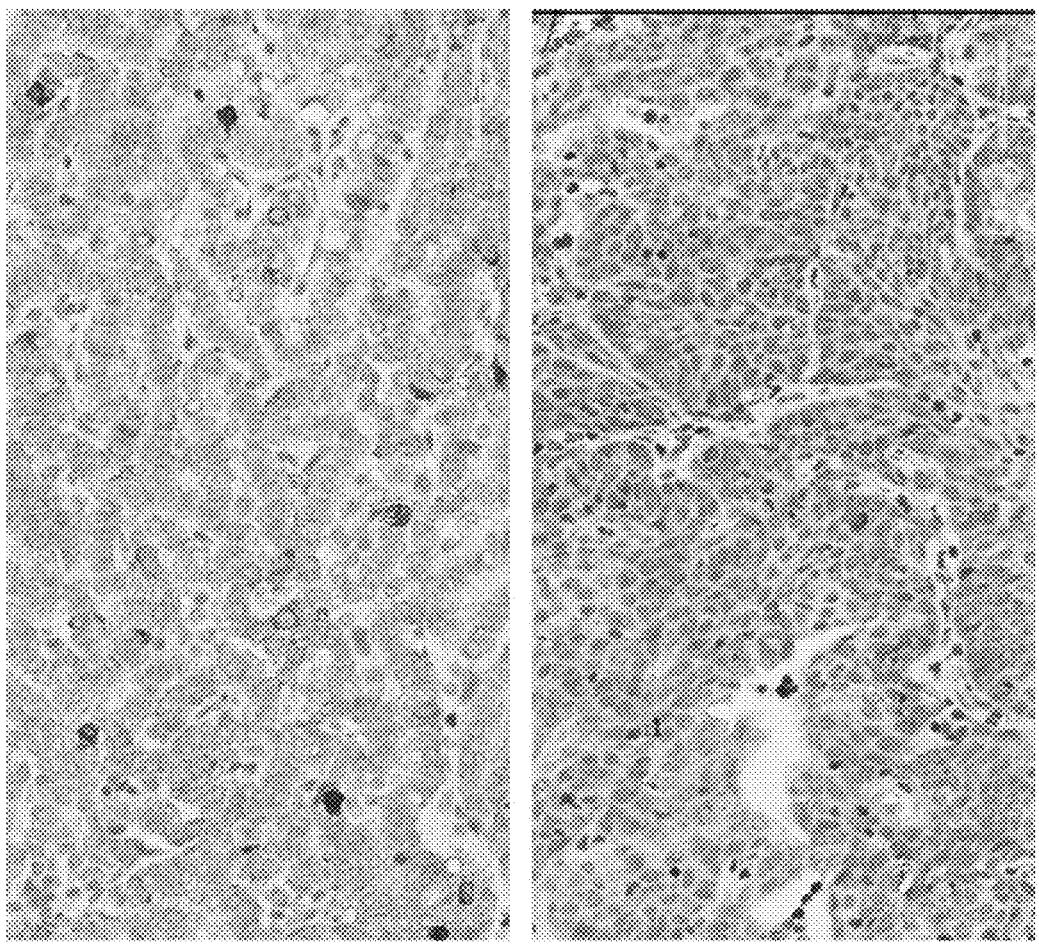
FIG. 5 depicts the immunohistochemistry of kidneys treated with exemplary micro-beads of the present invention using an antibody against an antigen on the surface of nanoparticles. The image shows diffuse tissue distribution of the beads (brown-colored sections).

Biodegradable microspheres containing nanoparticles were synthesized and injected into the systemic arterial system of rats. Animals were sacrificed later and kidneys were harvested as a sample of an end organ. Immunohistochemistry of the slides using antibody against an antigen on the surface of nanoparticles showed diffuse tissue distribution of the beads (brown-colored sections in FIG. 5).

Figure 6:
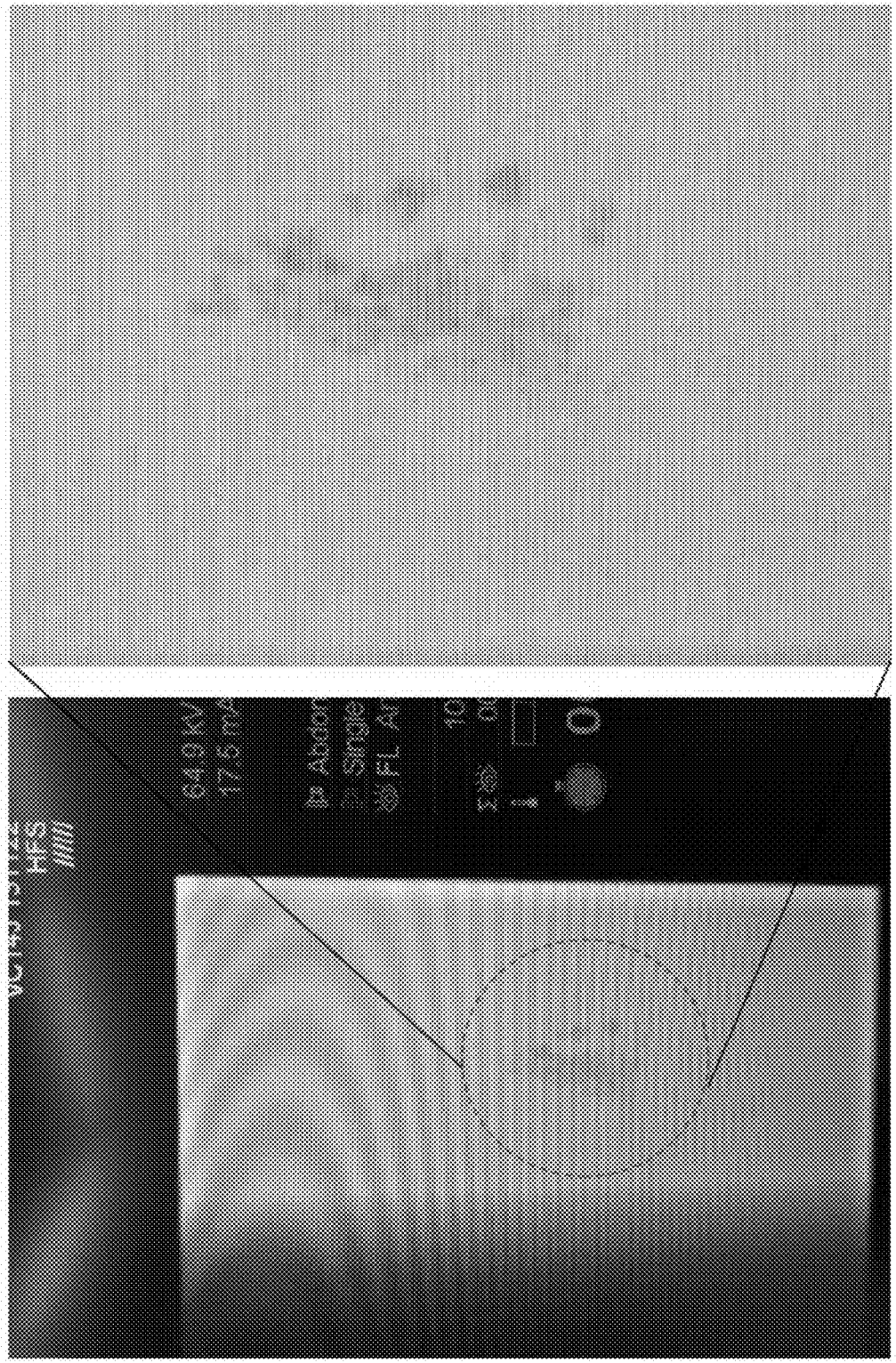
FIG. 6 is a photograph showing fluoroscopic imaging of radiopaque nano-beads encapsulated within exemplary micro-beads.

Fluoroscopic imaging: Radiopaque nanospheres were encapsulated within biodegradable microspheres and imaged under fluoroscopy (FIG. 6), demonstrating feasibility of real-time fluoroscopic imaging.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A micro-bead comprising:
   a matrix; and
   a plurality of nano-beads;
   wherein a surface of each said nano-bead of the plurality of nano-beads comprises a radionuclide, a lanthanide, or a trivalent cation that is linked to the surface of each said nano-bead by a chelator.

2. The micro-bead of claim 1, wherein the matrix comprises a polymer selected from the group consisting of polyglycolic acid (PG-A), polylactic acid (PLA), poly(lactic-co-glycolic acid) (PLGA), polycaprolactone (PCL), collagen, gelatin, glass, polymethylmethacrylate (PMMA), and polystyrene.

3. The micro-bead of claim 1, wherein the nano-beads comprise a polymer selected from the group consisting of poly(methyl methacrylate) (PMMA), polystyrene, carboxymethyl chitosan (CCN), PLGA, and carboxymethyl cellulose (CMC).

4. The micro-bead of claim 1, wherein the nano-beads comprise a biodegradable polymer.

5. The micro-bead of claim 1, wherein the nano-beads comprise a nonbiodegradable polymer.

6. The micro-bead of claim 1, wherein the nanobeads comprise the radionuclide that is linked to the surface of each said nano-bead by the chelator, wherein the radionuclide is a radioactive isotope of an element selected from the group consisting of actinium, astatine, bismuth, cesium, chromium, cobalt, dysprosium, erbium, holmium, iodine, iridium, iron, lead, lutetium, lutetium, molybdenum, palladium, phosphorus, potassium, radium, rhenium, samarium, selenium, sodium, strontium, sulfur, technetium, tritium, xenon, ytterbium, yttrium, carbon, nitrogen, oxygen, fluorine, copper, gadolinium, gallium, germanium, indium, krypton, rubidium, strontium, and thallium.

7. The micro-bead of claim 1, wherein the chelator is a radionuclide chelator selected from the group consisting of triethylenetetramine (TETA), 1,4, 7-triazacyclononane-1,4, 7-trisacetic acid (NOTA), and 1,4,7, 10-tetraazacyclododecane-1,4,7, 10-tetraacetic acid (DOTA).

8. The micro-bead of claim 1, wherein the nano-beads comprise a ligand selected from the group consisting of [$^{18}$F]altanserin, [$^{18}$F]setoperone, [$^{18}$F]ketanserin, [$^{18}$F]flumazenil, [$^{11}$C]3-amino-4-(2-dimethylaminomethylphenylsulfanyl)-benzonitrile ([$^{11}$C]DASB), [$^{11}$C]raclopride, [$^{123}$I]Ioflupane, and [$^{123}$I]Altropane.

9. The micro-bead of claim 1, wherein the nano-beads comprise an MRI contrast agent, a PET contrast agent, gold nanoparticles, color pigments, or a radiopaque contrast agent.

10. The micro-bead of claim 1, wherein the nano-beads further comprise boron-10 or gadolinium-157.

11. The micro-bead of claim 1, wherein the nano-beads comprise a chemotherapeutic agent selected from the group consisting of doxorubicin, cisplatin, taxol, vinblastine, vincristine, bleomycin, fluorouracil, methotrexate, bortezomib, and etoposide.

12. The micro-bead of claim 1, wherein the nano-beads comprise a cell-penetrating peptide selected from the group consisting of R9, TAT, HSV, gH625, penetratin, VP22, Xentry and transportan.

13. The micro-bead of claim 1, wherein the plurality of nano-beads comprise a polymer, a ligand, a chemotherapeutic agent, a metal, a color pigment, or a cell-penetrating peptide.

14. The micro-bead of claim 1, wherein the nanobeads comprise the lanthanide that is linked to the surface of each said nano-bead by the chelator, wherein the lanthanide is selected from samarium, gadolinium, dysprosium, holmium, erbium, ytterbium, and lutetium.

15. The micro-bead of claim 1, wherein the nanobeads comprise the trivalent cation that is linked to the surface of each said nano-bead by the chelator, wherein the trivalent cation is gadolinium (III).

16. A method of treating a disease or disorder in a subject, comprising:
   administering to the subject a composition comprising a plurality of micro-beads of claim 1.

17. The method of claim 16, wherein the micro-beads degrade over a period of time between 1 and 90 days.

18. The method of claim 16, wherein the disease or disorder is cancer.

19. The method of claim 18, wherein the cancer is selected from the group consisting of primary renal cell carcinoma (RCC), primary hepatocellular carcinoma (HCC), and liver metastatic lesions from other primary cancers.

20. The method of claim 19, wherein the cancer is liver metastatic lesions from other primary cancers selected from the group consisting of gastric cancer, colorectal cancer, breast cancer, pancreatic cancer, lung cancer, and prostate cancer.

21. A method of treating cancer in a subject in need thereof, the method comprising the steps of:
   administering to the subject a composition comprising the micro-bead of claim 10; and
   exposing the subject to a neutron source.

* * * * *